(12) United States Patent
Jiang et al.

(10) Patent No.: US 7,799,935 B2
(45) Date of Patent: Sep. 21, 2010

(54) CRYSTALLINE DULOXETINE HYDROCHLORIDE

(75) Inventors: Wei Ping Jiang, Chongqing (CN); Chun Rong Jia, Chongqing (CN)

(73) Assignees: Chongqing Shenghuaxi Pharmaceuticals Co. Ltd., Chongqing (CN); Arrow International Limited, Valetta (MT)

( * ) Notice: Subject to any disclaimer, the term of this patent is extended or adjusted under 35 U.S.C. 154(b) by 635 days.

(21) Appl. No.: 11/821,278

(22) Filed: Jun. 22, 2007

(65) Prior Publication Data

US 2008/0021089 A1  Jan. 24, 2008

(30) Foreign Application Priority Data

Jun. 23, 2006  (GB) ................................ 0612506.6

(51) Int. Cl.
    *C07D 333/36* (2006.01)
(52) U.S. Cl. ...................................................... 549/68
(58) Field of Classification Search .................... 549/68
    See application file for complete search history.

(56) References Cited

U.S. PATENT DOCUMENTS

| 4,956,388 A | 9/1990 | Robertson et al. |
| 5,023,269 A | 6/1991 | Robertson et al. |
| 5,362,886 A | 11/1994 | Berglund |
| 5,491,243 A | 2/1996 | Berglund |
| 2005/0197503 A1 | 9/2005 | Schiffers et al. |

FOREIGN PATENT DOCUMENTS

| EP | 1 820 800 A1 | 8/2007 |
| GB | 0612506.6 | 10/2006 |
| WO | WO 2005/019199 A1 | 3/2005 |
| WO | WO 2005/108386 A1 | 11/2005 |
| WO | WO 2006/055964 A2 | 5/2006 |
| WO | WO 2006/058121 A1 | 6/2006 |
| WO | WO 2006/081515 A2 | 8/2006 |
| WO | PCT/GB 2007/002325 | 8/2007 |
| WO | PCT/GB2007/002325 | 10/2008 |

OTHER PUBLICATIONS

Walter, W., "Lehrbuch der Organischen Chemie," 1988, S. Hirzel Verlag, Stuttgart, pp. 3-4, XP002454463.

Gao Li-mei, et al., "Synthesis of duloxetine hyydrochloride," Chinese Journal of New Drugs, vol. 14, No. 1, 2005, pp. 74-76, XP009088517.

Wheeler, W.J. et al., "An Asymmetric Synthesis of Duloxetine Hydrochloride, a Mixed Uptake Inhibitor of Serotonin and Norepinephrine, and its C-14 Labeled Isotopomers," Journal of Labelled Compounds and Radiopharmaceuticals, vol. XXXVI, No. 3, Aug. 1995, pp. 213-227, XP009019756.

Sython BV, "Duloxetine hydrochloride polymorphs," Research Disclosure, Kenneth Mason Publications Ltd., vol. DN498011, Oct. 2005, pp. 1129-1132, XP002394231.

*Primary Examiner*—Taofiq A Solola
(74) *Attorney, Agent, or Firm*—Sunstein Kann Murphy & Timbers LLP

(57) ABSTRACT

Crystalline duloxetine hydrochloride, compositions containing the same and methods for the production thereof.

25 Claims, 2 Drawing Sheets

CRYSTALLINE DULOXETINE HYDROCHLORIDE

CROSS-REFERENCE TO RELATED APPLICATIONS

This application claims priority from Great Britain Application Number GB 0612506.6, filed 23 Jun. 2006.

FIELD OF THE INVENTION

The present invention relates to crystalline duloxetine hydrochloride, to compositions containing the same and to methods for the formation thereof.

BACKGROUND OF THE INVENTION

Duloxetine hydrochloride is a potent dual reuptake inhibitor of serotonin and norepinephrine possessing comparable affinities in binding to serotonin and norepinephrine transport sites. Duloxetine hydrochloride has, therefore, been implicated in the treatment of various diseases related to these effects. For example, duloxetine hydrochloride is the active ingredient of the antidepressant drug Cymbalta® It is also used to target pain related to diabetic neuropathy and stress urinary incontinence.

Preparation of duloxetine hydrochloride has been disclosed elsewhere, for example in U.S. Pat. No. 5,023,269. Crystalline forms of the free base of duloxetine and their preparation have been reported in WO2005/108386. The amorphous form of duloxetine hydrochloride salt together with its preparation has been reported in WO2005/019199.

There is no generally applicable method for preparing a crystalline form of an amorphous drug. For example, it is impossible to know without experimentation whether any crystalline form of a given compound exists. Even once it has been found that a drug can be crystallised, extensive experimentation is usually required before a repeatable and quantifiable process is identified from which the crystalline form can be isolated. In this respect, several independently variable conditions, such as the nature of solvent, concentration of solvent and temperature, must be correctly identified in order to elucidate a suitable process. Indeed, to date, there have been no reports describing isolation or production of crystalline duloxetine hydrochloride.

It is, therefore, an object of the present invention to provide crystalline forms of duloxetine hydrochloride together with methods for the production thereof.

SUMMARY OF THE INVENTION

According to a first aspect of the present invention, there is provided crystalline duloxetine hydrochloride.

According to another aspect of the present invention, there is provided crystalline duloxetine hydrochloride which exhibits an X-ray diffraction pattern comprising peaks expressed in degrees two-theta at approximately 11.95±0.2, 21.44±0.2, 22.12±0.2, 23.08±0.2 and 24.06±0.2. The degree of error is preferably ±0.1.

According to a further aspect of the present invention, there is provided crystalline duloxetine hydrochloride which exhibits an X-ray diffraction pattern comprising peaks expressed in degrees two-theta at approximately 11.95±0.2, 13.93±0.2, 14.5±0.2, 14.76±0.2, 16.19±0.2, 17.97±0.2, 18.62±0.2, 18.82±0.2, 20.79±0.2, 21.26±0.2, 21.44±0.2, 21.76±0.2, 22.12±0.2, 22.28±0.2, 23.08±0.2, 23.28±0.2, 24.06±0.2, 26.31±0.2, 26.94±0.2 and 29.86±0.2. The degree of error is preferably ±0.1.

There is also provided by the present invention, crystalline duloxetine hydrochloride which exhibits an X-ray diffraction pattern substantially the same as shown in FIG. 1.

Preferably, the crystalline duloxetine hydrochloride has a purity of at least 95%, more preferably at least 98%.

According to a further aspect of the present invention, there is provided a method for the preparation of crystalline duloxetine hydrochloride, the method comprising:

(a) dissolving duloxetine in a first organic solvent to form a first solution;

(b) adding the first solution to a second organic solvent solution comprising HCl to form a second solution;

(c) adding the second solution to a third organic solvent to form a third solution;

(d) allowing duloxetine hydrochloride to crystallize out from the solution; and (e) collecting the crystallized duloxetine hydrochloride.

Preferably, the first organic solvent is a halogen substituted $C_1$ to $C_6$ hydrocarbon, more preferably dichloromethane.

In preferred embodiments, the second organic solvent is an alcohol, more preferably a straight or branched $C_1$ to $C_6$ alcohol, further preferably ethanol.

Preferably, the third organic solvent is a $C_1$ to $C_8$ hydrocarbon, more preferably hexane.

Preferably, the duloxetine is dissolved in the first organic solvent in a ratio of about 5 ml first organic solvent for about every 3 g of duloxetine.

In preferred aspects, the second organic solvent comprises about 20% HCl.

It is also preferred that the first solution is added to the second organic solvent at around 0° C. The first solution is preferably added to the second organic solvent with stirring.

Preferably, the second solution is added to a volume of the third organic solvent in a ratio of about 40 ml third organic solvent for about every 3 g duloxetine used in step (a).

In order to maximize crystallization, the duloxetine hydrochloride may be allowed to crystallize out from the solution during a period of cooling at around 0° C. to around 10° C. Preferably, the duloxetine hydrochloride is allowed to crystallize out from the solution during a period of about 10 hours.

Preferably, the crystallized duloxetine hydrochloride is collected by filtration. The collected crystallized duloxetine hydrochloride is preferably washed and then dried.

In preferred embodiments, the collected crystallized duloxetine hydrochloride is washed with a $C_1$ to $C_8$ hydrocarbon, more preferably hexane.

Preferably, the collected crystalline duloxetine hydrochloride is dried under vacuum.

Preferably, the method comprising the following additional steps for the preparation of duloxetine for use in step (a):

(i) placing duloxetine oxalate into a solution of a fourth organic solvent and water;

(ii) adding aqueous ammonia solution for dissolving the duloxetine oxalate;

(iii) isolating a separated organic layer;

(iv) washing the organic layer with saturated brine;

(v) drying the organic layer; and (vi) removing the solvents from the organic layer.

Preferably, the fourth organic solvent is a $C_1$ to $C_6$ ester, more preferably ethyl acetate.

The duloxetine oxalate is preferably placed into a solution of the fourth organic solvent and water at a ratio of about 300 ml fourth organic solvent and water solution for about every 39 g of duloxetine oxalate.

Preferably, the solution of a fourth organic solvent and water contains about 1 ml fourth organic solvent for about every 1 ml water.

The aqueous ammonia is preferably added under stirring.

Preferably, an aqueous layer is isolated and then washed with the fourth organic solvent.

According to a further aspect of the present invention, there is provided crystalline duloxetine hydrochloride prepared by any of the methods above.

Preferably, the crystalline duloxetine hydrochloride has a purity of at least 95%, more preferably at least 98%.

Accordingly, the present invention describes a novel crystalline form of duloxetine hydrochloride and a process to prepare it.

It is anticipated that the crystalline form of duloxetine hydrochloride disclosed herein will be useful in the treatment of a variety of diseases which are prevented, ameliorated or eliminated by the administration of a serotonin and/or norepinephrine reuptake inhibitor. Examples of such diseases include depression, pain related to diabetic neuropathy and stress urinary incontinence, obesity, alcoholism, loss of memory, anxiety and smoking.

According to another aspect of the present invention, there is therefore provided a pharmaceutical composition comprising crystalline duloxetine hydrochloride as described herein.

According to a further aspect, there is provided a composition for treating a disease which is prevented, ameliorated or eliminated by the administration of a serotonin and/or norepinephrine reuptake inhibitor, the composition comprising crystalline duloxetine hydrochloride as described herein.

Preferably, the disease is selected from depression, pain related to diabetic neuropathy and stress urinary incontinence, obesity, alcoholism, loss of memory, anxiety and smoking.

There is also provided a method of treating a disease which is prevented, ameliorated or eliminated by the administration of a serotonin and/or norepinephrine reuptake inhibitor, the method comprising administering to a patient a therapeutically effective amount of crystalline duloxetine hydrochloride as described herein, or of the pharmaceutical composition as described herein.

Preferably, the disease is selected from depression, pain related to diabetic neuropathy and stress urinary incontinence, obesity, alcoholism, loss of memory, anxiety and smoking.

By a therapeutically effective amount, it is meant an amount which is capable of preventing, ameliorating or eliminating the diseases mentioned herein.

The crystalline duloxetine hydrochloride can be mixed with a carrier, diluent or excipient therefor, all of which are well known in the art. For example, suitable carriers may include pills, powders, lozenges, sachets, cachets, elixirs, suspensions, emulsions, solutions, syrups, aerosols, ointments, soft and hard gelatine capsules, suppositories, sterile injectable solutions and sterile packaged powders.

There are many advantages to providing a crystalline form of duloxetine hydrochloride compared to an amorphous form. A crystalline form of the drug can be easily purified by crystallisation and recrystallisation. Compared to other methods of purification, it is also cheaper and more convenient to perform crystallisation on a large scale. Furthermore, a crystalline form may be more stable than an amorphous form.

BRIEF DESCRIPTION OF THE DRAWINGS

An example of the present invention will now be described in detail with reference the accompanying figures.

DETAILED DESCRIPTION OF THE INVENTION

Figure 1:
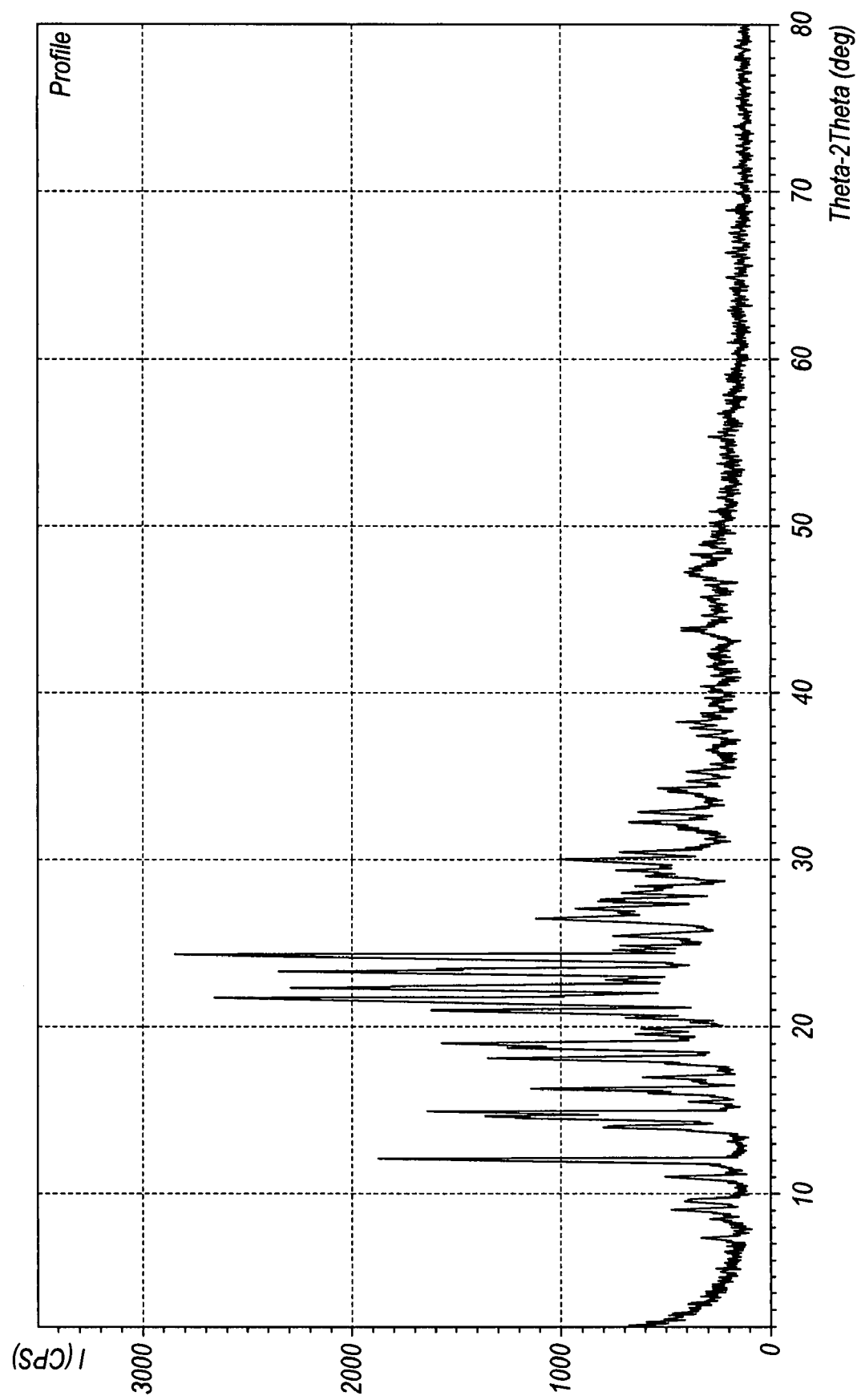
FIG. 1 shows the X-ray Diffractometer (XRD) spectrum for the crystalline form of the present invention.
Figure 2:
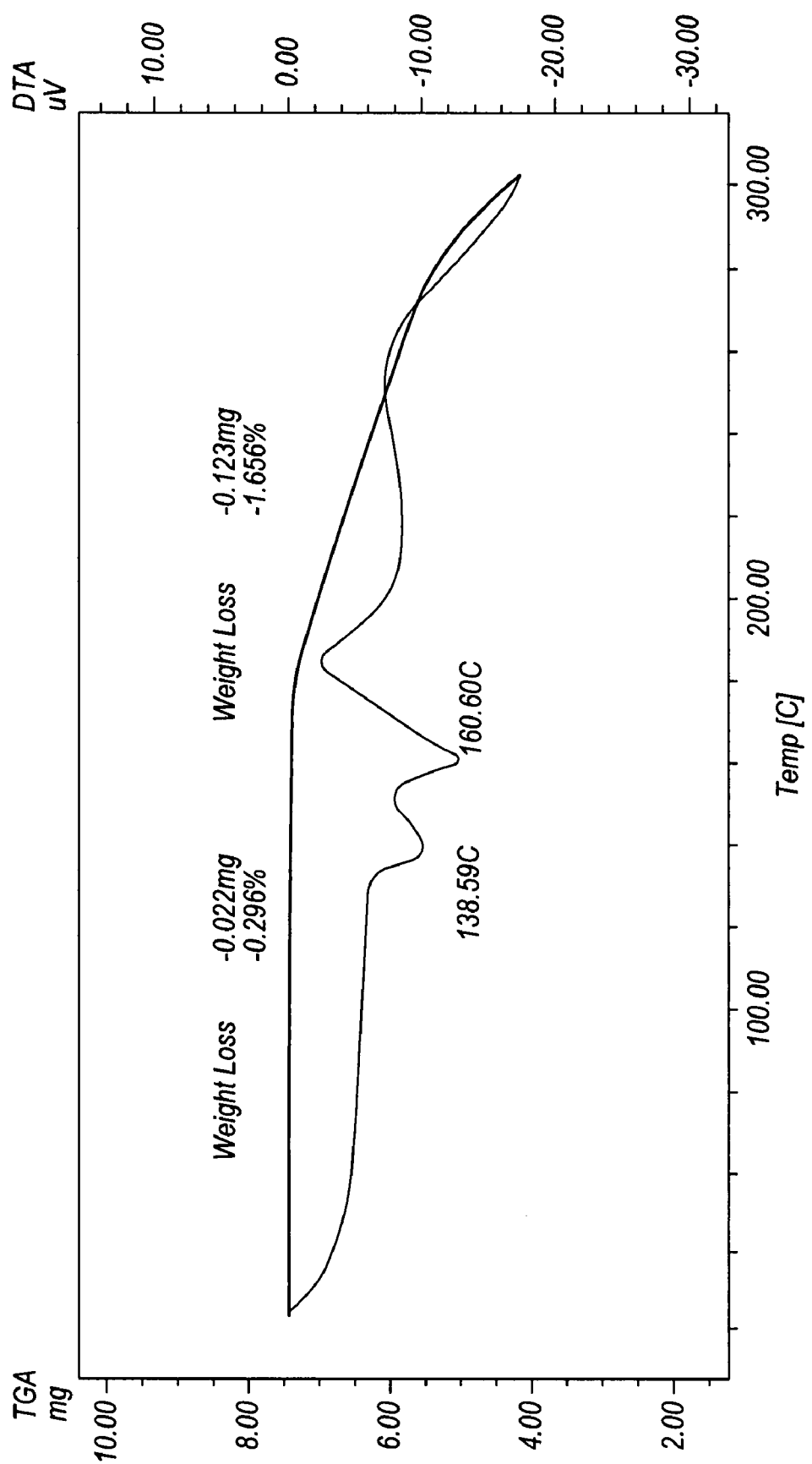
FIG. 2 shows Thermogravimetric Analysis (TGA) and Differential Thermal Analysis (DTA) thermograms for the crystalline form of the present invention.

Duloxetine oxalate salt was initially prepared following the procedure given in EP 273658 (corresponding to U.S. Pat. Nos. 5,023,269 and 4,956,388, each hereby incorporated by reference). Duloxetine was then freed from the oxalic acid and converted directly to its hydrochloride salt by the introduction of hydrochloride in organic solvent.

The isolated crystalline duloxetine hydrochloride was fully characterized by Differential Scanning Calorimetry (DSC), solid carbon-13 NMR and X-ray powder diffraction.

Crystallization

EXAMPLE 1

Free Duloxetine Preparation

Duloxetine oxalate (38.7 g) was placed into 300 ml of an ethyl acetate/water (1:1) mixture. Aqueous ammonium solution was added to dissolve the solid completely under stirring. The separated aqueous layer was washed with ethyl acetate twice. The combined organic solution was then washed with saturated brine, and dried with anhydrous sodium sulphate. The free duloxetine (26 g) was obtained as an oil by removing the solvents from the filtrate solution.

Crystallization of Duloxetine Hydrochloride:

The free duloxetine (3 g) was first dissolved in dichloromethane (5 ml), then an ethanol solution (2 ml) containing 20% HCl was added at 0° C. with stirring, followed by hexane (40 ml). The crystalline product came out after the solution was cooled at 0-10° C. for 10 hours. The product was collected by filtration, washed with hexane and dried (1.8 g, 55% yield, m.p. 148-154° C.). Its purity was 98.4% with an optical purity of 99.6%. The DTA result shown m.p. was 160.6° C. The crystalline form, designated as Form III, was thus obtained.

TABLE 1

The XRD spectrum for the crystalline form obtained according to Example 1.

| 2 theta (degree) | I/I$_0$ | D(A) |
| --- | --- | --- |
| 11.952 | 64 | 7.398 |
| 13.930 | 25 | 6.351 |
| 14.500 | 44 | 6.103 |
| 14.759 | 55 | 5.997 |
| 16.190 | 35 | 5.470 |
| 17.968 | 44 | 4.932 |
| 18.620 | 37 | 4.761 |
| 18.820 | 50 | 4.711 |
| 20.785 | 52 | 4.270 |
| 21.260 | 35 | 4.175 |
| 21.438 | 89 | 4.141 |
| 21.760 | 21 | 4.081 |
| 22.120 | 71 | 4.015 |

TABLE 1-continued

The XRD spectrum for the crystalline form obtained according to Example 1.

| 2 theta (degree) | I/I₀ | D(A) |
|---|---|---|
| 22.280 | 50 | 3.986 |
| 23.080 | 71 | 3.850 |
| 23.280 | 46 | 3.817 |
| 24.055 | 100 | 3.696 |
| 26.309 | 29 | 3.384 |
| 26.940 | 24 | 3.306 |
| 29.861 | 29 | 2.989 |

TABLE 2

| TGA/DTA parameters | |
|---|---|
| Detector | DTG-60H |
| Sample Weight | 7.428 mg |
| Temperature Rate | 10° C. |
| Hold Temperature | 300° C. |
| Hold Time | 0 min |

The invention claimed is:

1. A method for the preparation of crystalline duloxetine hydrochloride, the method comprising:
   (a) dissolving duloxetine in a first organic solvent to form a first solution;
   (b) adding the first solution to a second organic solvent solution comprising HCl to form a second solution;
   (c) adding the second solution to a third organic solvent to form a third solution;
   (d) allowing duloxetine hydrochloride to crystallize out from the solution; and
   (e) collecting the crystallized duloxetine hydrochloride, wherein the first organic solvent is a halogen substituted $C_1$ to $C_6$ hydrocarbon.

2. The method of claim 1, wherein the first organic solvent is dichloromethane.

3. The method of claim 1, wherein the second organic solvent is an alcohol.

4. The method of claim 3, wherein the second organic solvent is ethanol.

5. The method of claim 1, wherein the third organic solvent is a $C_1$ to $C_8$ hydrocarbon.

6. The method of claim 5, wherein the third organic solvent is hexane.

7. The method of claim 1, wherein the duloxetine is dissolved in the first organic solvent in a ratio of about 5 ml first organic solvent for about every 3 g of duloxetine.

8. The method of claim 1, wherein the second organic solvent comprises about 20% HCl.

9. The method of claim 1, wherein the first solution is added to the second organic solvent at around 0° C.

10. The method of claim 1, wherein the first solution is added to the second organic solvent with stirring.

11. The method of claim 1, wherein the second solution is added to a volume of the third organic solvent in a ratio of about 40 ml third organic solvent for about every 3 g of duloxetine used in step (a).

12. The method of claim 1, wherein the duloxetine hydrochloride is allowed to crystallize out from the solution during a period of cooling at around 0° C. to around 10° C.

13. The method of claim 1, wherein the duloxetine hydrochloride is allowed to crystallize out from the solution during a period of about 10 hours.

14. The method of claim 1, wherein the crystallized duloxetine hydrochloride is collected by filtration.

15. The method of claim 1, wherein the collected crystallized duloxetine hydrochloride is washed and then dried.

16. The method of claim 15, wherein the collected crystallized duloxetine hydrochloride is washed with a $C_1$ to $C_8$ hydrocarbon.

17. The method of claim 16, wherein the collected crystallized duloxetine hydrochloride is washed with hexane.

18. The method of claim 1, comprising the following additional steps for the preparation of duloxetine for use in step (a):
   (i) placing duloxetine oxalate into a solution of a fourth organic solvent and water;
   (ii) adding aqueous ammonia solution for dissolving the duloxetine oxalate;
   (iii) isolating a separated organic layer;
   (iv) washing the organic layer with saturated brine;
   (v) drying the organic layer; and
   (vi) removing the solvents from the organic layer.

19. The method of claim 18, wherein the fourth organic solvent is a $C_1$ to $C_6$ ester.

20. The method of claim 19, wherein the fourth organic solvent is ethyl acetate.

21. The method of claim 18, wherein duloxetine oxalate is placed into a solution of the fourth organic solvent and water at a ratio of about 300 ml fourth organic solvent and water solution for about every 39 g of duloxetine oxalate.

22. The method of claim 18, wherein the solution of a fourth organic solvent and water contains about 1 ml fourth organic solvent for about every 1ml water.

23. The method of claim 18, wherein the aqueous ammonia is added under stirring.

24. The method of claim 18, wherein an isolated aqueous layer is washed with the fourth organic solvent.

25. The method of claim 18, wherein the organic layer is dried with anhydrous sodium sulphate.

* * * * *